United States Patent [19]

Kampf et al.

[11] Patent Number: 4,503,964
[45] Date of Patent: Mar. 12, 1985

[54] SAMPLE HANDLING APPARATUS

[75] Inventors: Richard S. Kampf, Costa Mesa; Richard W. Winn, Orange, both of Calif.

[73] Assignee: Beckman Instruments, Inc., Fullerton, Calif.

[21] Appl. No.: 99,375

[22] Filed: Dec. 3, 1979

Related U.S. Application Data

[63] Continuation of Ser. No. 958,075, Nov. 6, 1978, abandoned, which is a continuation of Ser. No. 754,814, Dec. 27, 1976, abandoned.

[51] Int. Cl.³ ............................................. B65G 43/00
[52] U.S. Cl. ..................................... 198/341; 198/472
[58] Field of Search ............... 198/339, 341, 345, 470, 198/472, 466, 467, 580, 646, 648, 656, 793–795, 719, 722, 857; 73/421 R, 423 A, 864.91; 250/328; 414/222, 403, 422

[56] References Cited

U.S. PATENT DOCUMENTS

| | | | |
|---|---|---|---|
| 3,544,272 | 12/1970 | Vaills | 73/423 A |
| 3,859,528 | 1/1975 | Luitwieler et al. | 250/328 |
| 3,871,511 | 3/1975 | Wentz et al. | 198/470 |
| 4,001,585 | 1/1977 | Coutarel | 250/328 |
| 4,040,533 | 8/1977 | De Boer et al. | 198/472 |

Primary Examiner—Joseph E. Valenza
Attorney, Agent, or Firm—R. J. Steinmeyer; R. R. Meads; J. R. Shewmaker

[57] ABSTRACT

Sample handling apparatus for circulating one or more sample holders along a rectilinear path in a sample holder storage compartment and past an operating station at which the holders may be removed from and then returned to the compartment. First and second parallel conveyors on opposite sides of the operating station drive the holders toward and away from the operating station. Lateral drivers engage the holders in longitudinal stop positions at opposite ends of the conveyors and drive them laterally between conveyors to lateral stop positions, one of the holders during lateral movement being driven into and away from an operative position at the operating station. A movable sample compartment divider between the conveyors is indexed in synchronism with the lateral drivers to engage and stabilize the sample holder at the operating station. Circulation of the holders is monitored by proximity switches at the longitudinal stop positions, limit switches at the lateral stop positions, intermediate switches in each lateral path between conveyors, and an indexing switch actuated by the movable divider.

4 Claims, 8 Drawing Figures

SAMPLE HANDLING APPARATUS

This is a continuation of application Ser. No. 958,075, filed Nov. 6, 1978, now abandoned, which was a continuation of Ser. No. 754,814, filed Dec. 27, 1976, now abandoned.

BACKGROUND OF THE INVENTION

I. Field of the Invention

The present invention relates to sample handling apparatus and, more particularly, to apparatus for circulating sample holders in a storage compartment past an operating station. The invention is particularly well suited for handling samples which, after stabilization at the operating station, are removed from the storage compartment, operated upon, and then returned to the compartment.

II. Description of the Prior Art

U.S. Pat. No. 3,859,528 (Luitweiler et al., issued Jan. 7, 1975) illustrates a prior commercial sample handling apparatus for circulating a plurality of sample holding vials past an operating station. The vials are supported within respective compartments of multi-compartment sample holding trays and the trays are circulated in rectilinear fashion around the sample storage compartment of the apparatus. At the operation station an elevator removes a vial, positions it in a radiation detection chamber for analysis, and then returns the vial to the compartment. To this end the sample storage compartment is loaded with two longitudinally extending, generally parallel columns of trays on opposite sides of the operating station. Longitudinally movable fingers at opposite ends of each column increment the entire column of trays longitudinally a distance of one tray depth to drive trays in the first column toward the operating station and trays in the second column away from the operating station. After incrementing each column of trays, trays at the remote ends of the columns are indexed laterally from one column to the other after which the fingers again increment the columns one tray depth.

While the foregoing apparatus functions reasonably well for the purpose intended, it suffers from a number of inherent drawbacks which reduce its overall commercial attractiveness. First, because of the limited longitudinal drive capabilities of the incrementing fingers, incremental movement of each tray column requires that each tray abut an adjacent tray so that the trays can increment each other serially in domino fashion. As a result, if the apparatus does not contain a full load of trays, the incrementing fingers are unable to longitudinally increment the tray columns to positions wherein the trays at the remote ends of the columns may be laterally indexed between columns. In addition, when indexing, the apparatus may fail to accurately align a tray in position over the elevator at the operating station. In such a case the elevator, instead of engaging and removing the sample vial, will instead strike the tray and cause the apparatus to jam. Further, there is no provision in the prior apparatus for detecting or signalling the occurrence of the foregoing malfunctions.

In copending U.S. application Ser. No. 754,815, now abandoned for "Sample Handling Apparatus" filed concurrently herewith in the name of Richard S. Kampf, a novel sample handling apparatus is disclosed which is capable of circulating any number of sample holders from one to a full load. The apparatus also is capable of accurately stabilizing each holder as it moves to and away from and while at an operating station. To these ends, the apparatus includes first and second parallel conveyor means or opposite sides of the operating station for conveying sample holders in first and second opposite directions toward and away from the station. Means are also included at the remote end of each conveyor for halting motion of the sample holders in first and second longitudinal stop positions for subsequent lateral movement of the end-most sample holders between the conveyors. During such lateral movement, one of the holders is moved into position at the operating station and indexing means is provided for then engaging and stabilizing the holder during operation of the station.

While the apparatus of the copending application is a substantial improvement over prior apparatus, even it may be subjected to operating problems. For example, it is possible in the apparatus for a sample holder on a conveyor not to fully seat in its longitudinal stop position for subsequent lateral movement by lateral drive means. If such occurs, the holder and lateral drive means may be misaligned, and the lateral drive means may improperly engage and tip over or otherwise disturb the position of the holder. Also, in the apparatus, the operating station is capable of operating when the indexing means is not fully engaged with a sample holder at the station. If such operation occurs, it is possible that the station may jam or otherwise disturb the position of the holder in an undesirable manner.

In addition to overcoming the foregoing possible problems, it is, of course, desirable that such a sample handling apparatus include improved means for increasing the speed with which samples may be transported for processing while maintaining the stable transport thereof.

SUMMARY OF THE INVENTION

The present invention resides in novel and improved sample handling apparatus which circulates sample holders in a rectilinear path past an operating station. The apparatus includes first and second conveyor means on opposite sides of the station for conveying sample holders longitudinally in first and second opposite directions toward and away from the operating station to first and second longitudinal stop positions. The apparatus also includes first and second lateral drive means for laterally moving each sample holder in the first and second longitudinal stop positions between the first and second conveyor means.

In accordance with an important aspect of the invention, first and second proximity switch means at opposite ends of the first and second conveyor means detect the presence of a sample holder proximate the longitudinal stop positions and in combination with control means drive the first and second conveyor means for a limited period following actuation of the proximity switch means. With this arrangement, the sample holders are driven completely to the longitudinal stop positions and cannot stop at some point just prior thereto. This assures proper engagement of the sample holders with the lateral drive means.

In accordance with another aspect of the invention, each sample holder is engaged and stabilized in position at the operating station by indexing means, and further switch means is provided to monitor operation of the indexing means and to energize the operating station only when the indexing means is in position to fully engage and stabilize the sample holder. In the preferred embodiment, the indexing means is a movable sample holder compartment divider which is movable into a position engaging and stabilizing the sample holder, and the switch means is actuated by the divider in such position. In this manner, the station is only operated on proper positioning of the indexing means, and hence on proper positioning of the sample holder, thereby avoiding jamming of the operating station.

In accordance with another aspect of the invention, intermediate switch means in each lateral path further serve to ensure that the conveyor means are disabled while a sample holder is being moved laterally. In addition, the intermediate switch means in the first lateral path adjacent the operating station enables the operating station only if the sample holder is present in the first lateral path. With this arrangement, if no sample holder is present in the first lateral path but one is present in the second lateral path, the operating station will be inhibited and the latter sample holder will be rapidly moved along the second lateral path without the delay associated with operation of the station.

In accordance with another aspect of the invention, control means is provided responsive to operation of the first and second switch means indicative of a sample holder in a longitudinal stop position for inhibiting the first and second conveyor means. The control means further includes limit switch means indicative of the presence of a holder in a lateral stop position on the first conveyor means and override means responsive to actuation of the limit switch means by a sample holder for driving said conveyor means until a sample holder actuates the first switch means in the first longitudinal stop position irrespective of any actuation of the second switch means. With such an arrangement, if a sample holder arrives at the lateral stop position on the first conveyor means, the first conveyor means will be enabled until a sample holder reaches the first longitudinal stop position thereof for increment past the operating station irrespective of the arrival of a sample holder at the second longitudinal stop position at the end of the second conveyor means.

DESCRIPTION OF THE PREFERRED EMBODIMENT

Figure 1:
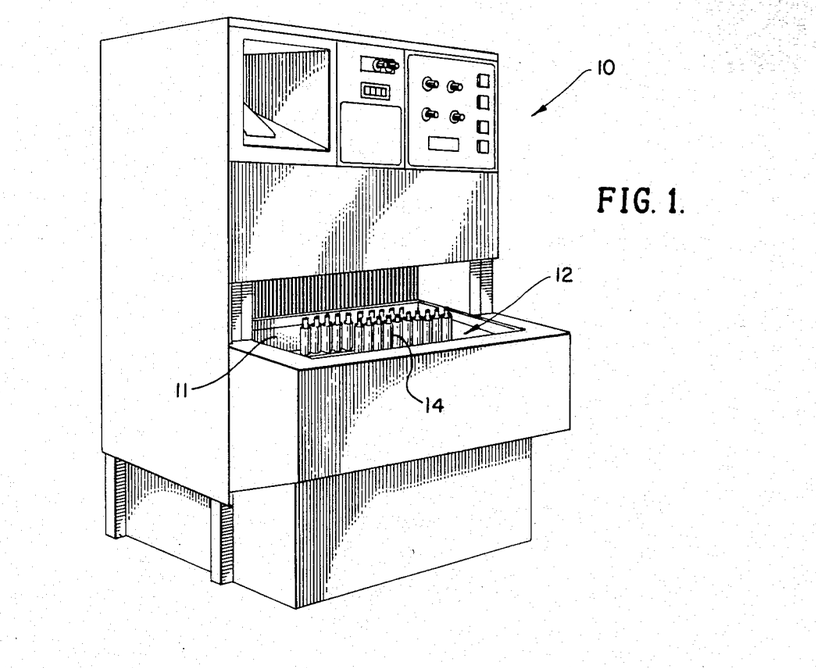
FIG. 1 is a perspective view of an analytical instrument incorporating the sample handling apparatus of the present invention and illustrates sample holders in position for circulation by the apparatus.

Referring now to the drawings, FIG. 1 illustrates a radiation measuring analyzer 10 including a generally rectangular sample holder storage compartment 11 supporting a plurality of sample holders 14. In addition, the analyzer incorporates sample handling apparatus 12 for circulating the sample holders 14 along a rectilinear path past an operating station 28 (see FIGS. 5 and 7) of the analyzer. The analyzer may be of the type which transfers samples from the operating station to a radiation detection chamber, measures radioactive emissions, such as gamma emissions, from the sample, and then returns the sample to the sample handling apparatus 12. Common instruments of this type include gamma counters, liquid scintillation counters, and the like. For example, the aforementioned U.S. Pat. No. 3,859,528 illustrates a gamma counting system for which the sample handling apparatus of the invention is particularly suited.

Figures 2, 3:
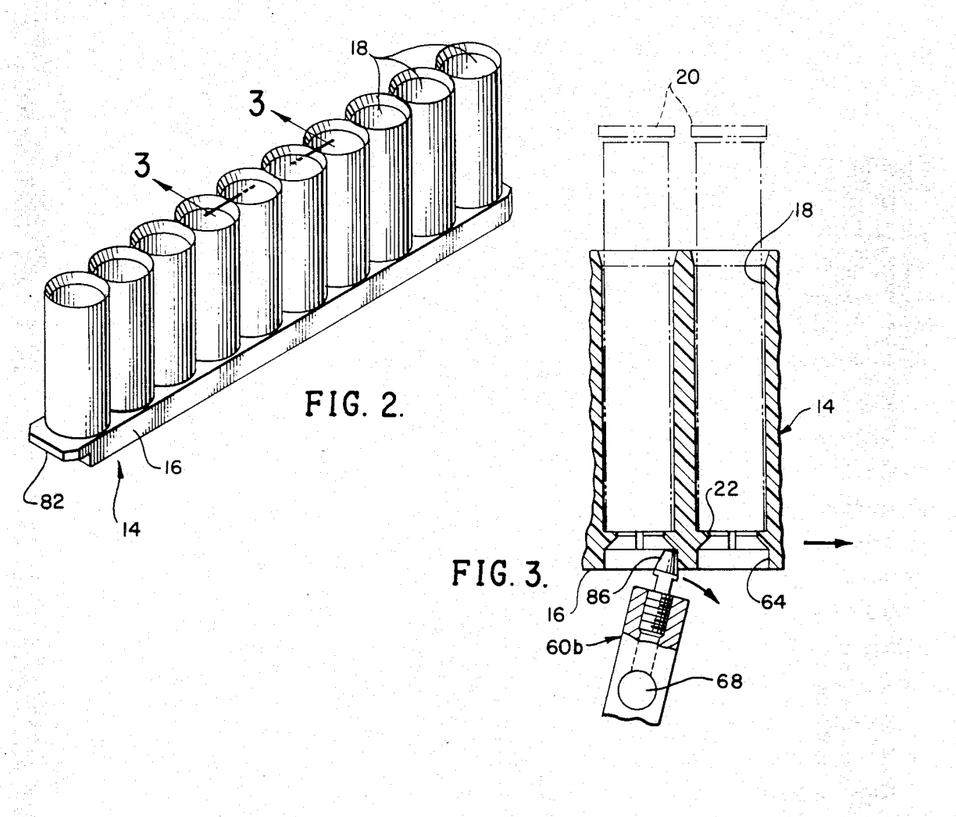
FIG. 2 is a perspective view of a sample holder for use with the sample handling apparatus.
FIG. 3 is a sectional view, taken along lines 3—3, of the sample holder in FIG. 2 and illustrates the compartmented structure of the sample holder with sample holding vials in each compartment, and additionally illustrates a lateral driver engaging the underside of the sample holder for moving the holder in accordance with the present invention.
Figure 7:
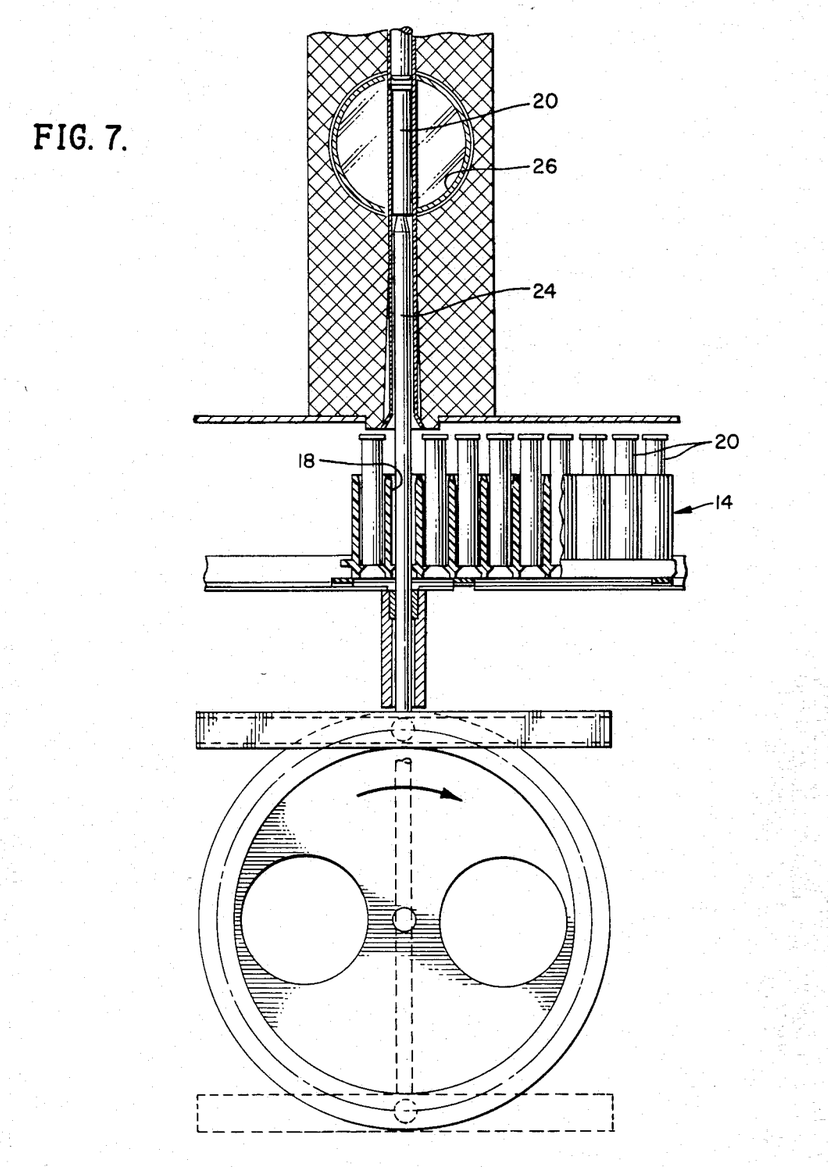
FIG. 7 is a fragmentary sectional view, taken in a generally vertical plane, through the sample handling apparatus of the invention and the radiation detection chamber of the analyzer of FIG. 1 and illustrates the positioning of a sample holder vial in the radiation counting chamber by an elevator mechanism extending through the sample handling apparatus into the chamber.

FIGS. 2 and 3 illustrate a suitable sample holder 14, of one piece construction, having a generally rectangular base 16 supporting a series of upstanding, generally cylindrical sample holding compartments 18 each of which may receive and support a sample holding vial or container 20. In this regard, each compartment includes an open bottom in the base 16 and an inwardly extending annular rib 22 for engaging and supporting the bottom of a vial 20 in the compartment. In the analyzer 10, when the sample holder 14 is positioned at the operating station 28, a sample holding compartment 18 and the corresponding sample holding vial 20 are positioned over an elevator rod 24 adapted to extend upwardly through the open bottom of the sample compartment to remove the vial therefrom. In this regard, FIG. 7 illustrates a typical elevator 24 such as found in the aforementioned patent, for lifting the sample holding vial 20 into a radiation detection chamber 26 of the analyzer 10. This elevator is conventional in design and reference is made to the aforementioned patent for additional details regarding the operation thereof. Briefly, the elevator rod 24, which is normally in a lowered position beneath the sample holder storage compartment 11 at the operating station 28, is illustrated in a raised position extending vertically upward through the sample holding compartment 18 to support the vial 20 in the detection chamber 26 for analyses. After the sample in the vial 20 is counted in the chamber 26, the elevator rod 24 is lowered to return the vial to sample holding compartment 18, and the sample holder 14 is moved laterally to position another sample at the operation station for analysis.

Figure 5:
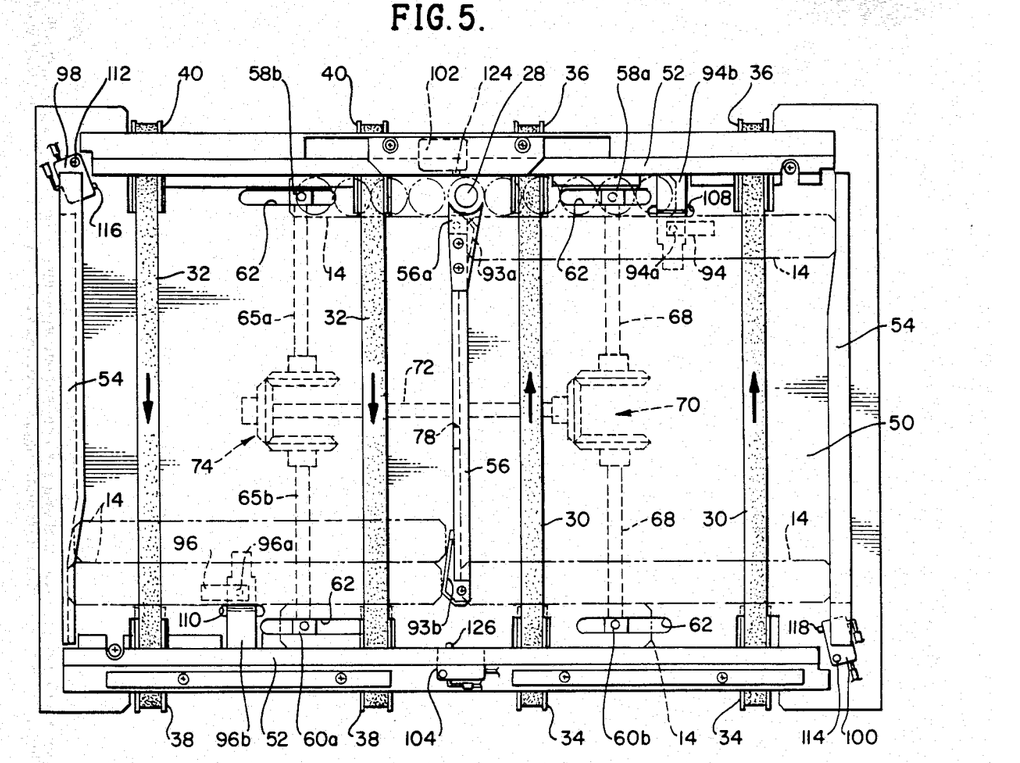
FIG. 5 is a top plan view of the sample handling apparatus of FIG. 4 and illustrates in phantom outline sample holders positioned for movement longitudinally by conveyor means and laterally by lateral drive means.

In the analyzer 10 such lateral movement of the sample holder 14 is under control of the sample handling apparatus 12. In accordance with one important aspect of the present invention, the sample handling apparatus is designed to circulate along a rectilinear path any desired number of sample holders 14 from one up to a full load for the storage compartment 11. Generally speaking, to accomplish this, the sample handling apparatus 12 includes first and second parallel conveying means which engage and drive the sample holders in first and second opposite directions toward and away from the operating station 28. As shown in FIG. 5, the first conveying means includes a pair of conveyor belts 30 on which the sample holders 14 ae supported for horizontal movement in the direction of the arrows toward the operating station. The second conveyor means includes a second pair of conveyor belts 32, generally parallel to belts 30, and on which sample holders 14 are supported for horizontal movement in the opposite direction away from the operating station. The two conveyors 30 and 32 thus frictionally engage and drive sample holders in opposite longitudinal directions in a horizontal plane. The first sample holders on the first and second conveyors are driven until arriving at first and second longitudinal stop positions at the end of the respective conveyors. After the first sample holder on the conveyor 30 arrives at the first longitudinal stop position, it is stepped laterally by lateral drive means (to be described hereinafter) between the conveyors 30 and 32 past the operating station 28. During such stepping motion, the conveyors 30 and 32 are disabled and each vial 20 in the holder is positioned in sequence at the operating station for analysis as previously described. Similarly, the first sample holder 14 at the second longitudinal stop position is laterally stepped between conveyors 32 and 30 in synchronism with movement of the sample holder past the operating station. At the end of such lateral movement, the first sample holders reach first and second lateral stop positions on the conveyors 32 and 30 respectively. The conveyors 30 and 32 are then again enabled to drive a next pair of sample holders 14 to the first and second longitudinal stop positions for lateral stepping between the conveyors. Such rectilinear circulation of sample holders in a counterclockwise direction along and between the two conveyors continues during operation of the sample handling apparatus 12 for one up to a full load of sample holders. In this regard, a full load is the maximum number of sample holders on each conveyor 30 and 32 minus one sample holder on each conveyor to allow for shifting of holders between conveyors.

Figure 4:
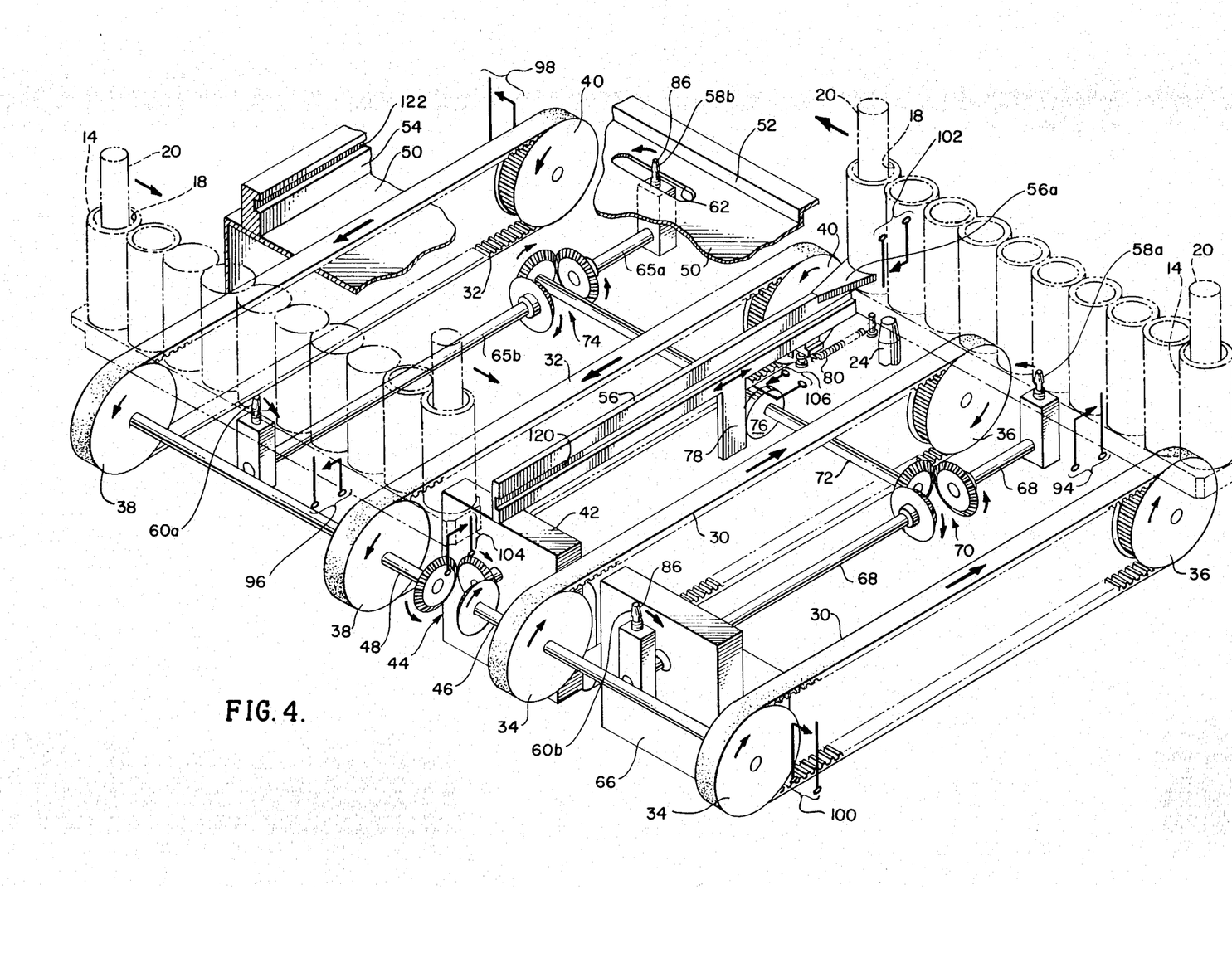
FIG. 4 is a perspective, broken away view illustrating the sample handling apparatus of the present invention and illustrates in phantom outline a first sample holder in position at an operating station and a second sample holder in a longitudinal stop position.

Turning now to a more detailed description of the illustrated sample handling apparatus 12 and referring to FIG. 4, the conveyor belts 30 of the first conveyor means are driven by a pair of motor driven pulleys 34 and pass around a pair of idler pulleys 36 at opposite ends thereof. Similarly, belts 32 of the second conveyor means are driven by motor driven pulleys 38 and pass around respective idler pulleys 40 at their opposite ends. Simultaneous motive power for the belts is provided by a common conveyor motor 42 coupled in a conventional manner through a set of three miter gears 44 to drive respective drive shafts 46 and 48 of pulleys 34 and 38 in opposite directions. By such a drive configuration, the belts 30 are driven in a first longitudinal direction while the belts 32 are driven in a second and opposite longitudinal direction.

In so moving, the upper exposed portions of the belts 30 and 32 ride on a bottom 50 of the sample holder storage compartment 11. To reduce friction between the belts and the bottom 50, strips of low friction plastic tape may be secured to the bottom 50 such that the underside of the exposed portions of the belts ride on the plastic tape.

The perimeter of the sample holder storage compartment 11 is bounded by vertical sides or shoulders which cooperate to limit the extent of travel of the sample holders 14 and to guide the holders during travel. Thus, at the opposite ends of the conveyor belts, laterally extending shoulders 52 function as stops to halt movement of a sample holder being conveyed when the holder strikes such end stop. In FIG. 4, the two sample holders shown in phantom outline are both situated adjacent respective lateral shoulders 52. Lateral shoulders 52, in addition to functioning as stops for conveyed holders, serve to guide the holders during lateral movement between the first and second conveyors.

Longitudinal sides of the sample holder storage compartment 11 are likewise bounded by shoulders 54 which may perform similar functions. Thus, shoulders 54 may function as stops to halt lateral movement of sample holders between conveyors and, in addition, may function to guide the sample holders during conveyance by conveyors 30 and 32.

A similar guiding function is performed by longitudinally extending center divider 56 positioned between and generally parallel to the conveyors 30 and 32.

As previously indicated, the sample holders 14 upon reaching the first and second longitudinal stop positions (defined by shoulders 52) at the ends of the first and second conveyors respectively, are stepped laterally between the conveyors by first and second lateral drive means. In a preferred form, such first and second lateral drive means comprise rotatable kicker assemblies 58a, 58b and 60a, 60b at opposite ends of the conveyor belts 30 and 32.

Figure 6:
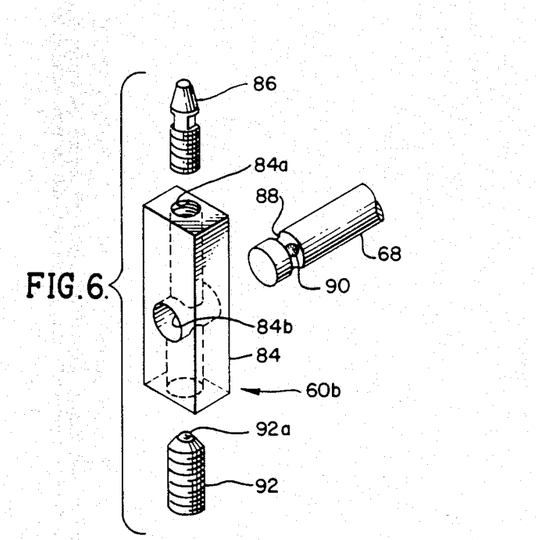
FIG. 6 is an exploded perspective view illustrating the torque limiting mechanism incorporated in the lateral drive means of the invention.

Each kicker assembly, as illustrated in the exploded view of one such assembly in FIG. 6, includes a kicker body 84 having a longitudinal bore 84a extending throughout the length thereof. The assembly further includes a kicker pin 86 which is threaded into one end of longitudinal bore 84a and which engages the shoulders 64 (FIG. 3) of sample holders 14 during kicker rotation. A kicker drive shaft 68 includes a circumferential annular groove 88 having a single detent 90 formed therein. The drive shaft is received within transverse bore 84b with groove 88 aligned with longitudinal bore 84a. Drive shaft 68 is coupled to the kicker body 84 by means of locking pin 92 threaded into the opposite end of bore 84a. The locking pin includes a plunger ball 92a at one end thereof which is spring loaded by a spring (not shown) within pin 92. When the locking pin is threaded into bore 84a, plunger 92a seats in detent 90 of drive shaft 68 and secures the drive shaft and the kicker assembly together. If the torque applied by the drive shaft exceeds a predetermined value, the spring loaded plunger 92a pops out of detent 90 and rides freely in annular groove 88 thereby removing the driving torque from the kicker assembly. This torque limiting feature is important since it removes driving torque from the sample holder by disengaging the drive shaft and the kicker assembly if the holder jams in the lateral path thereby preventing damage to the samples and overloading of the driving mechanism.

The kicker assemblies are disposed beneath the bottom 50 of the sample holder storage compartment 11 and during a fraction of each revolution the tip ends thereof protrude up through associated slots 62 in the bottom 50 to engage one of a series of equally spaced interior shoulders 64 on the bottom of the base 16 of a sample holder 14 as illustrated in FIG. 3. After engaging the shoulders in this manner, the kickers further rotate to step the holders laterally a distance substantially equal to the distance between adjacent compartments 18. This is repeated upon each revolution of the kicker assemblies with the kickers engaging successive shoulders 64 to laterally step the holder in the first and second longitudinal stop positions between the conveyors and first and second lateral stop positions.

Significantly, the kicker assemblies are adjustable to adjust the distance which a sample holder 14 is laterally stepped. For this purpose, the protruding length of the kicker pins (e.g. pin 86, FIG. 6) is adjustable by threading the pin further into or out of bore 84a. Increasing the protruding length of kicker pin 86 increases the lateral distance the kicker will drive the sample holder. Thus, the pin length may be precisely adjusted to the requisite length for bringing successive compartments 18 of the sample holder into position at the operating station 28.

As shown in FIG. 4, motive power for rotating the pairs of kickers 58 and 60 is provided by a common lateral drive motor 66. A drive shaft 68 of the motor 66 is coupled at one end to rotate kicker 60b in a clockwise direction and is coupled in a conventional manner at its other end through a set of three miter gears 70 to rotate kicker 58a in a counterclockwise direction. The middle of the three miter gears 70 is connected to a laterally extending shaft 72 having its opposite end connected to the middle of another conventional set of three miter gears 74. As illustrated, the remaining two miter gears of the set 74 are coupled in a conventional manner by driven shafts 65a and 65b to rotate kicker 58b in a counterclockwise direction and kicker 60a in a clockwise direction. With such a drive arrangement, all kickers are rotated in synchronism by the motor 66, kickers 58a and 58b rotating counterclockwise to laterally step the sample holder in the first longitudinal step position from the first conveyor, past the operating station to the second conveyor and kickers 60b and 60a rotating clockwise to step the sample holder in the second longitudinal stop position from the second to the first conveyor.

In accordance with an important aspect of the present invention, the sample holder 14 is engaged and stabilized in an operative position at the operating station 28 by indexing action of the sample compartment center divider 56. Structured as shown in FIG. 4 the divider 56 is movable longitudinally back and forth between a first position at which a forward end 56a of the divider proximate the operating station 28 engages and stabilizes sample holder 14 and a second position retracted from the sample holder permitting lateral movement of the holder between the conveyors 30 and 32. The means for supporting the divider 56 for such movement are conventional and for the sake of clarity are not shown in the drawings. However, longitudinal movement of the divider 56 is controlled by an eccentric 76 supported on the laterally extending drive shaft 72 which engages a downwardly extending arm 78 of the divider. A coil spring 80, connected between the divider and a frame member of the analyzer, normally spring loads the divider into its first position to engage and stabilize a sample holder in position at the operating station and against lateral shoulder 52. To permit lateral movement of the holder after operation of the station, shaft 72 rotates eccentric 76 which cams the divider into its second or retracted position (to the left in FIG. 4) away from the sample holder. FIG. 4 illustrates the divider in the retracted position.

The operation to laterally move a sample holder 14 begins with the center divider 56 in its first position engaging the sample holder and with the protruding pins (86, FIG. 6) of the kicker assemblies pointed downwardly. Lateral drive motor is energized to drive shaft 72 and eccentric 76 thereon to begin retracting divider 56. Simultaneously, the kicker assemblies 58-60 are rotated to drive the kicker pins 86 toward a position pointing upwardly as illustrated in FIG. 4. In this position, the kicker pin of assembly 58a will engage an associated shoulder 64 (FIG. 3) on the sample holder. Also, divider 56 will have been retracted thereby permitting lateral movement of the holder.

From the position illustrated in FIG. 4, the lateral drive motor continues to drive the kicker assembly which laterally shifts the sample holder until the next compartment 18 thereof is positioned at the operating station 28. The kicker assembly then disengages from the holder and continues rotating toward its initial position pointing downwardly. Simultaneously, rotating eccentric 76 permits center divider 56 to move toward its first position under the action of spring 80. At the end of the operation, the center divider will be in its first position (FIG. 5) engaging and stabilizing the sample holder 14 while the kicker assemblies will have reached their initial position pointed downwardly.

The end 56a of divider 56 engaging the sample holder has a concave circular configuration which engages the mating cylindrical exterior surface of the sample holder compartments 18 to securely lock the sample holder in position.

By virtue of the indexing arrangement for stabilizing the holder 14 in operative position at the station 28 the holder is first positively stepped into the proper position and is second securely engaged and maintained in this position. As a result, the possibility of the elevator rod 24 striking and jamming on an improperly positioned holder is eliminated.

In addition, to further stabilize and guide a sample holder 14 during movement along each lateral path, the lateral shoulders 52 may each include a laterally extending tongue or lip (not shown) which extends horizontally over the top surface of base 16 of the sample holder to help prevent tipping or vertical movement of the holder while in the lateral path.

Tipping of sample holders during conveyance along conveyors 30 and 32 is similarly precluded by a tongue and groove arrangement between the sample holder 14 and the sample handling apparatus 12. For this purpose the base 16 of the sample holder 14 has a tongue 82 extending from one end thereof (FIG. 2) which engages a mating groove 120 extending along one longitudinal side of sample compartment center divider 56 (FIG. 4) during conveyance by the first conveyor 30. During conveyance by the second conveyor 32, tongue 82 engages groove 122 in longitudinally extending shouler 54 (FIG. 4). Alternatively, instead of a tongue 82 the holder could have a groove which mated with associated tongues extending from the divider 56 and the shoulder 54. In any event, with the tongue and groove engagement on each conveyor, the sample holder 14 cannot tip forward or backward in the longitudinal direction. This is particularly important when only a few sample holders are being circulated and there are no adjacent holders to prevent tipping. In addition, by providing the tongue and groove arrangement at only one and the same longitudinal edge of each conveyor (e.g. the left longitudinal edge of each as viewed in FIG. 4), the sample holders 14 can only be positioned on each conveyor in the same lateral direction. This ensures that all holders in the compartment 11 are oriented identically. As a result, the compartments 18 of each sample holder are shifted past the operating station in the same order starting at the same end of each holder.

At the opposite ends of first and second conveyors, sample holders are shifted slightly outward as they are driven into the respective longitudinal stop positions by the conveyors. For this purpose, referring to FIG. 5, upstanding camming surfaces 93a (dashed outline) and 93b are disposed near the end of and adjacent the interior longitudinal side of each conveyor. When a sample holder reaches the camming surface it is cammed outwardly. The longitudinal shoulders 54 of the sample compartment are recessed at the end of each conveyor, as illustrated in FIG. 5, to permit the slight lateral outward shift of the sample holders by the camming surfaces.

In the present invention, circulation of sample holders 14 by the sample handling apparatus 12 is monitored and controlled by a plurality of switches associated with the apparatus and which are illustrated diagrammatically in FIG. 4. These include a pair of longitudinal stop switches 94 and 96 disposed at the longitudinal stop positions associated with conveyor belts 30 and 32 respectively. Switches 94 and 96 are actuated by the presence of sample holders in the first and second longitudinal stop positions respectively and function to inhibit operation of the conveyors 30 and 32 during lateral stepping of the holders between conveyors. Similarly, lateral stop switches 98 and 100 are disposed at the ends of respective lateral paths. Such limit switches are actuated by the presence of sample holders in first and second lateral stop positions and function to inhibit operation of the lateral driving kicker assemblies 58 and 60 prior to conveyance of the sample holders along conveyors 30 and 32. Intermediate switches 102 and 104 are disposed in the first and second lateral paths between conveyors. Intermediate switch 102 is actuated by the presence of a sample holder at the operating station 28, while switch 104 is actuated by a sample holder in a corresponding position along the second lateral path. An indexing switch 106 actuated by the presence of the divider 56 in its first position provides a count of samples processed as well as an indication of the accurate positioning of a sample holder at the operating station.

In a preferred form of the invention, longitudinal stop switches 94 and 96 are proximity switches which are actuated by a sample holder 14 prior to reaching its respective longitudinal stop position. Further, means are preferably included for driving the conveyors for a limited period of time after actuation of a proximity switch, the period being sufficient to ensure that the sample holder is fully seated in its longitudinal stop position. For this purpose and as shown in FIG. 5, proximity switch 94 includes a microswitch contact 94a (in dashed outline) situated beneath the bottom 50 of the storage compartment 11. An actuating arm 94b for the microswitch extends upwardly through a slot 108 in the bottom 50 and extends horizontally from the slot to the lateral shoulder 52 at the end of the first conveyor 30. When a sample holder reaches the slot 108, it engages and depresses contact arm 94b to actuate the switch 94.

The switch 94 is coupled to control circuitry for driving the conveyor 30 for a period of time sufficient to ensure that the sample holder is driven and fully seated in a longitudinal stop position against shoulder 52. A period of two seconds is sufficient for this purpose. It should be noted that a sample holder will engage the arm 94b and actuate the proximity switch prior to reaching a position over rotating kicker 58a. Actuation of the proximity switch 94 always drives the holder to the shoulder 52, so that in this manner a holder cannot stop prematurely in a position misaligned from the kicker 58a. This prevents possible jamming or tipping of the holder during rotation of the kicker 58a as might occur if the kicker and the holder were not properly aligned for lateral stepping movement.

Proximity switch 96 is identical in structure and operation to switch 94. Thus, it includes a contact 96a beneath bottom plate 50 and an actuating arm 96b extending upwardly through a slot 110 and extending horizontally to shoulder 52.

The lateral stop switches 98 and 100, referring to the plan view of FIG. 5, are mounted at the ends of the first and second lateral paths by means of vertical pins 112 and 114 respectively about which the switches can rotate in a horizontal plane. The switches are spring biased into positions as shown having respective contact arms 116 and 118 positioned away from shoulders 54 of the sample compartment. When a sample holder 14 is laterally shifted by a kicker assembly, it engages the contact arm of the associated lateral stop switch thereby actuating the switch which supplies a signal to disable the lateral drive motor 66 and hence disable the kicker assemblies. The holder may continue lateral movement briefly after actuating the contact arm of the lateral stop switch, in which case the holder rotates the associated switch about the axis of pin 112 or 114 back toward shoulder 54 against the action of the bias spring. This provides a degree of tolerance in the lateral position at which the holder finally stops. In most cases it is possible to seat the holder in a lateral stop position without the holder striking the shoulder 54. However, the shoulder 54 may, if necessary, actually stop the holder after the lateral drive motor is disabled as well as establish the limit of the lateral stop position.

The intermediate switches 102 and 104, still referring to FIG. 5, include associated contact arms 124 and 126 which protrude outwardly from laterally extending shoulders 52 into the lateral paths between the conveyors 30 and 32. Contact arm 124 of first intermediate switch 102 is disposed in the first lateral path at the operating station 28 and is actuated by a sample holder 14 when any of its compartments 18 are positioned at the operating station. Contact arm 126 of second intermediate switch is disposed at a corresponding position in the second lateral path and is actuated by a holder 14 being shifted in the second lateral path.

Indexing switch 106 (FIG. 4) is disposed beneath bottom 50 of the storage compartment and includes a contact arm (not shown) which is contacted and actuated by arm 78 depending from center divider 56 when the divider is in its first position for engaging and stabilizing a holder 14 at the operating station. When divider 56 is retracted, it disengages from the contact arm of index switch 106. If desired, switch 106 may be positioned to be actuated by other elements of the lateral drive means. For example, switch 106 could be positioned adjacent a cam (not shown) on lateral drive motor shaft 68. The contact arm of the switch would be actuated once during each revolution of the shaft. With this modification switch 106 would continue to indicate the number of revolutions of shaft 68 and the kicker assemblies and hence provide control for a counter counting the number of sample compartments 18 positioned at the operating station 28. However, switch 106 would not then respond directly to movement of the center divider 56 into position for stabilizing a sample holder at the operating station, so that actuation of the switch would not be in direct response to and hence a direct indication of the movement of divider 56 into its first position for engaging and stabilizing the sample holder.

Figure 8:
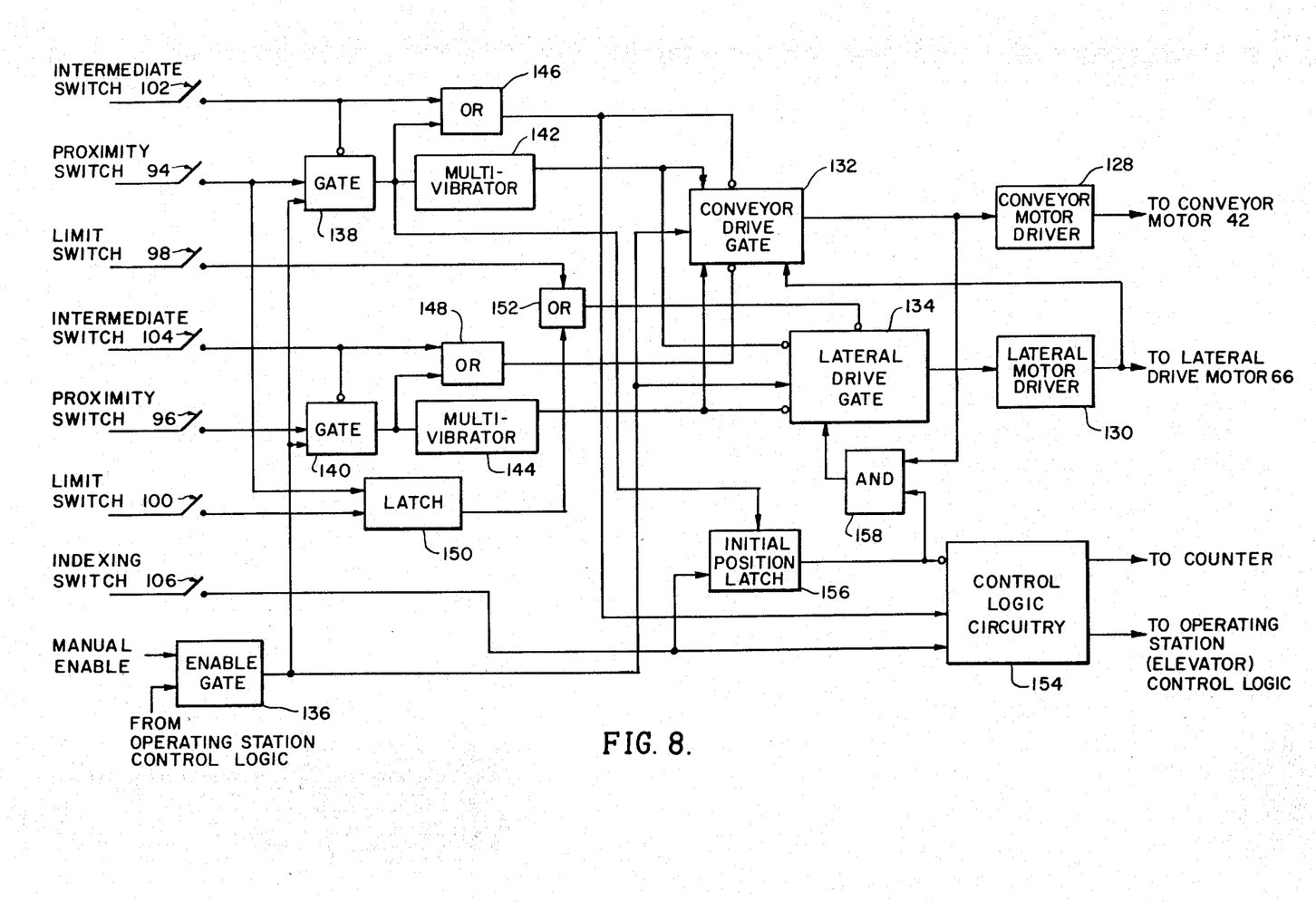
FIG. 8 is a block diagram of the control circuitry of the sample handling apparatus.

Various forms of conventional control circuitry may be employed to control the sample handling apparatus 12 in response to operation of the aforementioned switches. Accordingly it is by way of example only that FIG. 8 illustrates one form of a logic block diagram of the electrical control circuitry for controlling the conveyor motor 42 and the lateral drive motor 66 in response to action of the aforementioned switches. In that regard, conveyor drive motor 42 and lateral drive motor 66 are driven by electrical signals from conventional conveyor and lateral motor drivers 128 and 130, respectively. The conveyor and lateral drivers in turn are controlled by respective conveyor drive and lateral drive gates 132 and 134 which supply enable or inhibit signals to the conveyor and lateral drivers in response to control signals received from selected ones of switches 94–106. Unless otherwise disabled, the conveyor drive and lateral drive gates 132 and 134 are conditioned to enable their respective drive motor 42 and 66 by input signals received from the output of an engine gate 136. Enable gate 136 responds to signals from conventional control logic (not shown) controlling elevator 24 to condition motor drive gates 132 and 134 after the elevator returns a sample container 20 to sample holder 24.

As control inputs to the conveyor and lateral drive gates 132 and 134, the control logic includes logic gates 138 and 140, "one-shot" multivibrators 142 and 144, OR gates 146 and 148, latch 150, and a further OR gate 152. In a conventional manner, input connections to these and other logic elements are illustrated as enabling inputs unless they inhibit or disable the logic element in which case the input connection thereto is illustrated with a circle.

Proximity switch 94, at the longitudinal stop position of the first conveyor 30, supplies an enabling input to logic gate 138, while intermediate switch 102 in the first lateral path at the operating station 28 supplies a disabling input to this gate. The output of gate 138 is connected to trigger "one-shot" multivibrator 142 which, in turn, has its output supplied as an enabling input to conveyor drive logic 132 and as a disabling input to lateral drive logic 134.

OR gate 146 receives input signals from either intermediate switch 102 or from proximity switch 94 (through gate 138), and OR gate 146 supplies a disabling input to conveyor drive logic 132.

In a similar manner, proximity switch 96 at the longitudinal stop position of the second conveyor 32 supplies an enabling input to logic gate 140, while intermediate switch 104 in the second lateral path supplies a disabling input thereto. The output of logic gate 140, in turn, is connected to actuate "one-shot" multivibrator 144 which, like multivibrator 142, supplies an enabling input to conveyor drive logic 132 and a disabling input to lateral drive logic 134.

OR gate 148 receives input signals from either intermediate switch 104 in the second lateral path or from proximity switch 96 (through gate 140) at the end of the second conveyor. OR gate 148, like OR gate 146, supplies a disabling input to conveyor drive gate 132.

Lateral drive gate 134 for controlling the lateral drive motor 66 is coupled to receive disabling input signals from each of multivibrators 142 and 144. In addition, lateral drive gate 134 is disabled by actuation of either first or second lateral stop position limit switch 98 or 100 which are connected to input terminals of OR gate 152. The output of OR gate 152 is supplied as the disabled input to the lateral drive gate 134.

Control logic 154 is provided having a first output for supplying signals controlling a counter (not shown) for counting the samples operated on at the operating station 28 and a second output for supplying signals to conventional system control circuitry for controlling the operation of the elevator and other apparatus at the operating station. Control logic circuitry 154 receives an enabling input from indexing switch 106 and a second enabling input from the output of OR gate 146. (The OR gate output indicates actuation of either or both of proximity switch 94 at the first longitudinal stop position or intermediate switch 102 at the operating station.) With this arrangement, actuation of switches 94 or 102, indicating presence of a sample holder in the first lateral path, together with actuation of switch 106 when the center divider 56 is in position for stabilizing a sample holder, will condition control circuitry 154 to enable the elevator drive logic for removing a sample container 20 for analysis and to enable the counter for counting the samples processed.

In the preferred embodiment, the counter is incremented by one after the sample is returned to the holder 14 from the radiation chamber 26 by the actuation of switch 106 stabilizing the next sample to be processed at the operating station. Thus, in order to preclude incrementing the counter when the first sample is originally positioned at the operating station 28, an initial position latch 156 is provided which receives a set input from proximity switch 94 (through gate 138). When set, initial position latch 156 supplies a disabling input to the control logic 154 for disabling the counter. Thus, when the first sample is positioned at the operating station and indexing switch 106 closes, the counter is disabled. When the second sample is positioned at the station, indexing switch 106 resets initial position latch 156 to enable the counter so that the first sample is then counted, and so on for succeeding samples.

The output of the initial position latch 156 is also connected to one input of AND gate 158, the outer input of which is received from conveyor drive logic 132. When the conveyor drive logic 132 disables the conveyor motor, the output from gate 132 is coupled through AND gate 158 to enable the lateral drive gate 134. Similarly, the enabled output of lateral motor driver 130 is connected as a disabling input to the conveyor drive logic 132. With these arrangements, the conveyor motor 42 and lateral drive motor 66 are not energized simultaneously.

In operation, and assuming that one sample holder 14 is in the sample compartment 11 and is positioned on the first conveyor 30, an output signal from enable gate 136 enables the conveyor drive logic 132 which signals conveyor motor driver 128 to drive the conveyors 30 and 32. The holder 14 is conveyed until it actuates proximity switch 94 just prior to reaching the longitudinal stop position at the end of the first conveyor. The signal from switch 94 is applied through gate 138 to trigger multivibrator 142 which supplies an output pulse of predetermined duration, for example two seconds, which enables the conveyor drive logic for this duration. The signal from proximity switch 94 is further supplied through OR gate 146 to disable the conveyor drive logic 132. However, the multivibrator output overrides this disable signal thereby driving the conveyor for a predetermined period after actuation of proximity switch 94. Upon termination of the output pulse from multivibrator 142, the associated enable signal is removed from conveyor drive logic 132, and the disable signal from proximity switch 94 (switch 94 is still actuated by the sample holder) is supplied through gate 146 to logic 132 to then inhibit operation of the conveyor. This is an important feature which ensures that the conveyors 30 and 32 are driven for a limited period of time sufficient to fully seat the holders in a longitudinal stop position.

The actuation of proximity switch 94, in addition to inhibiting the conveyor motor 42, also serves to enable the lateral drive motor 66. In this regard, actuation of proximity switch 94 sets initial position latch 156. With this latch set, the lateral drive logic 134 for enabling the lateral drive motor is enabled through gate 158 upon receipt by gate 158 of a conveyor inhibited output signal from the conveyor drive logic 132.

When lateral drive motor 66 is enabled, the kicker assemblies are driven through one rotation to laterally shift the holder 14 to position the first compartment 18 thereof over the elevator 24 at the operating station 28. Actuation of indexing switch 106, upon proper positioning of center divider 56 to engage and stabilize the sample holder, resets the initial position latch 156 and conditions control logic 154 to actuate the conventional control circuitry for initiating operation of elevator 34 for removing a sample container 20 from the sample holder for analysis. This is an important feature which ensures that the elevator 24 is only actuated if the center divider 56 is in position for engaging and stabilizing the holder, thereby avoiding possible jamming or other malfunctions at the operating station.

When the sample container 20 has been returned to the sample holder 14, the elevator control logic supplies an enable signal through enable gate 136 to initiate another lateral shift of the sample holder 14 one sample position. At this time, the conveyor drive logic remains disabled due to continued actuation of either or both of switches 94 and 102 by holder 14.

When the second sample is moved into position at the operating station, closure of switch 106 in response to movement of center divider 56 against the sample holder, conditions control logic 154 to increment the counter by one for the first sample counted and to enable the elevator drive logic a second time to remove the second sample container from the holder for analysis.

The holder 14 is laterally shifted in this manner by the pair of rotating kicker assemblies 58 until the holder actuates limit switch 98 in the first lateral stop position. Actuation of switch 98 supplies a disable signal through OR gate 152 to the lateral drive logic 134 which disables the lateral drive motor 66. Simultaneously, when the holder leaves the operating station 28, intermediate switch 102 is opened thereby removing the disable signal applied therefrom through OR gate 146 to the conveyor drive logic 132. As a result, the conveyor drive logic enables the conveyor drive motor 42.

The sample holder is then conveyed along the second conveyor 32 until it actuates the proximity switch 96 proximate the second longitudinal stop position at the end of the second conveyor. Actuation of proximity switch 96 triggers multivibrator 144 through gate 140 to supply an enable signal to the conveyor drive logic in a manner identical to that supplied upon actuation of proximity switch 94. Thus, the conveyor is driven for a predetermined duration to ensure that the holder is seated in the second longitudinal stop position. Upon termination of the output pulse from multivibrator 144, the conveyor drive logic 132 is disabled by a signal supplied through OR gate 148 from either of proximity switch 96 or intermediate switch 104.

When the conveyor is thus inhibited, the lateral drive logic 134 is enabled through gate 158 to begin laterally shifting the holder 14 in the second lateral path from conveyor 32 to conveyor 30. This lateral movement proceeds in a manner similar to lateral shifting in the first lateral path past the operating station. However, if a holder is only present in the second lateral path and not in the first lateral path, switches 94 and 102 in the first lateral path are not actuated. Therefore these switches do not supply an enable input to control logic 154 for counting samples and for controlling elevator operation. As a result, as a holder is shifted only in the second lateral path, each time switch 106 closes it conditions control logic 154 to immediately supply an enable signal to the gate 136 to initiate another shifting action. This action shifts the holder along the second lateral path without the delays associated with operation of the operating station.

When the holder 14 reaches the second lateral stop position over the first conveyor 30 and actuates limit switch 100, switch 100 sets latch 150 which supplies a disable signal to the lateral drive logic 134 through OR gate 153 to disable the lateral drive motor 66. Simultaneously, the final lateral shift of holder 14 opens intermediate switch 104 in the second lateral path. Opening switch 104 removes the disable signal applied therefrom through OR gate 148 to the conveyor drive logic 132. As a result, the conveyor drive logic is enabled and the sample holder is again driven toward the first longitudinal stop position on the first conveyor 30.

Significantly, latch 150 has a reset input terminal connected to proximity switch 94 so that the latch is reset only upon actuation of switch 94 by the arrival of a sample holder at the first longitudinal stop position. Thus, the inhibiting output from latch 150 supplies to the lateral drive logic 134 through OR gate 152 remains until a sample holder on the first conveyor 30 reaches the first longitudinal stop position. As a result, since proximity switches 94, 96 and intermediate switches 102, 104 are open, the conveyor drive logic is enabled and drives until a holder on the first conveyor reaches the first longitudinal stop position. This is important when another holder is present on the second conveyor 32 which could reach the second longitudinal stop position and actuate proximity switch 96 (thereby disabling the conveyors) before a holder on the first conveyor has reached the first longitudinal stop position. Thus, if after latch 150 has been actuated, a sample holder on the second conveyor reaches the second longitudinal stop position and actuates proximity switch 96, the conveyors will not stop but will continue to drive until a holder reaches the first longitudinal stop position and actuates proximity switch 94. In such circumstance, actuation of proximity switch 96 is overriden. This is an important feature which ensures that sample holders are moved toward the operating station as expeditiously as possible.

Operation with more than one sample holder in the sample compartment is identical to the above operation If, when the apparatus is first turned on, sample holders are in position in either lateral path, thereby actuating one or both of intermediate switches 102 or 104, the intermediate switches apply disable signals to respective logic gates 138 and 140 to condition the logic gates to inhibit multivibrators 142 and 144. Thus, the multivibrators cannot be triggered to drive the conveyors with holders in one or both of the lateral paths.

Similarly, when the apparatus is turned on, sample holders may be in position to actuate proximity switches 94 or 96 but not fully seated in the first or second longitudinal stop positions. In order to fully seat such holders, the enable signal from enable gate is supplied to logic gates 138 and 140 to trigger multivibrator 142 or 144 (if proximity switch 94 or 96 is also actuated) to enable the conveyor drive for a limited period to fully seat the holders in the longitudinal stop positions.

While a preferred embodiment of the invention has been illustrated and described, it will be apparent that various modifications may be made therein without departing from the spirit and scope of the invention as defined in the appended claims.

What is claimed is:

1. In apparatus for circulating sample holders in a sample holder storage compartment along a rectilinear path past an operating station at which a sample carried by said holder is operated upon, said apparatus of the type including first and second substantially parallel conveyor means on opposite sides of said operating station for engaging and driving sample holders positioned thereon in first and second opposite directions toward and away from said station, first and second stops adjacent opposite ends of said first and second conveyor means for halting motion of said sample holders in said first and second directions, respectively, to define first and second longitudinal stop positions on said conveyor means for each holder, the improvement comprising: proximity switch means proximate each respective longitudinal stop position for indicating the presence of a sample holder on said conveyor means proximate but prior to reaching a respective longitudinal stop position as well as at said longitudinal stop position, and control means responsive to the actuation of said proximity switch means for inhibiting said first and second conveyor means after driving said first and second conveyor means for a limited duration following actuation of said proximity switch means to drive a sample holder for a limited period of time sufficient to reach its corresponding longitudinal stop position on said conveyor means against the corresponding stop; and first and second lateral drive means for engaging each sample holder in said first and second longitudinal stop positions and for laterally moving said holders between said first and second conveyor means only after the inhibition of said first and second conveyor means, said first lateral drive means laterally moving its associated sample holder into and then away from an operative position adjacent said station.

2. The apparatus of claim 1 wherein said control means includes: means responsive to actuation of said proximity switch means for generating a control signal of said limited duration; means connected between said generating means and said first and second conveyor means for supplying said control signal as a driving input signal to said conveyor means to drive same for said limited duration; and means for supplying an inhibit input signal to said conveyor means upon termination of said control signal to inhibit driving of said conveyor means.

3. In apparatus for circulating sample holders along a rectilinear path past an operating station in a sample holder storage compartment, said apparatus of the type including first and second substantially parallel conveyor means on opposite sides of said operating station for engaging and driving sample holders in first and second opposite directions toward and away from said station, first and second means adjacent opposite ends of said first and second conveyor means for halting motion of said sample holders in said first and second directions respectively to define first and second longitudinal stop positions for each holder and including first and second control switch means responsive to the presence of sample holders in said first and second longitudinal stop positions, first and second lateral drive means for engaging each sample holder in said first and second longitudinal stop positions and for laterally moving said holders between said first and second conveyor means toward first and second lateral stop positions on said second and first conveyor means, respectively, said first lateral drive means laterally moving its associated sample holder into and then away from an operative position adjacent said station, control means responsive to operation of said first and second control switch means indicative of a sample holder in a longitudinal stop position for inhibiting said first and second conveyor means, the improvement comprising: said control means further including limit switch means indicative of the presence of a sample holder in said second lateral stop position on said first conveyor means, override means responsive to actuation of said limit switch means by a sample holder in said second lateral stop position for driving said conveyor means until a sample holder on said first conveyor means actuates said first control switch means in said first longitudinal stop position irrespective of any interim actuation of said second control switch means by a sample holder on said second conveyor means in said second longitudinal stop position.

4. Apparatus for circulating sample holders along a rectilinear path past an operating station in a sample holder storage compartment, said apparatus of the type including first and second substantially parallel conveyor means on opposite sides of said operating station for engaging and driving sample holders in first and second opposite directions toward and away from said station, first and second means adjacent opposite ends of said first and second conveyor means for halting motion of sample holders in said first and second directions respectively to define first and second longitudinal stop positions for each holder, first and second lateral drive means for engaging each sample holder in said first and second longitudinal stop positions and for laterally moving said holders along respective first and second lateral paths between said first and second conveyor means, said first lateral drive means laterally moving its associated sample holder along said first lateral path into and away from an operative position adjacent said station, the improvement comprising: switch means in each lateral path responsive to the presence of a sample holder in a respective lateral path; and means responsive to the operation of said switch means indicative of no sample holder in said first lateral path adjacent said operating station for inhibiting operation of said operating station and for conditioning said lateral drive means, if operation of said switch means is indicative of a sample holder in said second lateral path, to move such latter sample holder along said second lateral path, whereby such holder is moved along the second lateral path without the delays associated with operation of the operating station.

* * * * *